United States Patent [19]

Segawa

[11] Patent Number: 5,667,477
[45] Date of Patent: Sep. 16, 1997

[54] INNER STRUCTURE OF ENDOSCOPE

[75] Inventor: Youichi Segawa, Omiya, Japan

[73] Assignee: Fuji Photo Optical Co., Ltd., Saitama, Japan

[21] Appl. No.: 593,681

[22] Filed: Jan. 29, 1996

[30] Foreign Application Priority Data

Feb. 14, 1995 [JP] Japan ................................. 7-025484

[51] Int. Cl.$^6$ ................................................. A61B 1/00
[52] U.S. Cl. ..................... 600/153; 600/101; 600/104; 600/130
[58] Field of Search .................... 600/101, 104, 600/106, 130, 131, 153, 154, 156; 604/280, 283

[56] References Cited

U.S. PATENT DOCUMENTS 4,972,828  11/1990  Ito .................................. 600/153

*Primary Examiner*—Beverly M. Flanagan
*Attorney, Agent, or Firm*—Oliff & Berridge

[57] ABSTRACT

A tube is inserted into a second connecting member and the second connecting member is moved toward a joint ring along the tube. Then the second connecting member is housed in a housing space of the joint ring to secure a length L2 required for a connecting operation. Next, the first connecting member is pushed into the tube. Then the second connecting member is moved from the housing space along the tube so as to be coupled with the second connecting member. The tube is held between the first and the second connecting members. As a result, the length L2 of the space for connecting the pipe and the tube can be larger than the conventional length L1 by the length L3 by which the second connecting member is housed in the housing space.

11 Claims, 6 Drawing Sheets

INNER STRUCTURE OF ENDOSCOPE

BACKGROUND OF THE INVENTION

1. Field of The Invention

The present invention relates to an inner structure of an endoscope and more particularly to an inner structure of an operation section which includes a forceps opening for guiding a medical treatment means such as a biopsy forceps.

2. Description of The Related Art

FIG. 5 shows an inner structure of a conventional endoscope. As shown in the drawing, an operation section 3 includes a forceps opening 1 which communicates with the end of an insertion part 5 which is inserted into the interior of a human body via a pipe 2 and a tube 4. The pipe 2 and the tube 4 are connected to each other by a first connecting member 6 which is cylindrical and has a convex(T)-shape in cross section, and the second connecting member 7. The first connecting member 6 is secured to the end of the pipe 2. The tube 4 is made to pass through the second connecting member 7.

In order that the pipe 2 and the tube 4 are connected to each other, the second connecting member 7 is retracted in such a manner to contact with a joint 9 as shown in FIG. 6. Then, the end of the tube 4 is coupled to a projected portion 6A of the first connecting member 6. Then, the second connecting member 7 is moved toward the first connecting member 6 along the tube 4, and the first connecting member 6 is screwed in the second connecting member 7. The tube 4 is held between the projected portion of the first connecting member 6 and a ring 7A of the second connecting member 7. As a result, the pipe 2 and the tube 4 are connected to each other. The above-described connecting process is generally carried out by handwork at the time of manufacturing.

The insertion part 5 is connected to the operation section 3 by the joint 9. An inner space 9A is formed inside the joint 9. The above-mentioned tube 4, an image bundle in the case of a fiber scope, and an electric cable in an electronic endoscope, etc. pass through the inner space 9A.

In the case of the conventional structure for the operation section of an endoscope, a space for connecting the pipe 2 to the tube 4 is restricted by a length L1 from a right end 7B of the second connecting member 7 of which left end is in contact with an end surface 9B of the joint 9, to a left end of the projected portion 6A as shown in FIG. 6.

Under the conventional condition, the length L1 is too short to perform the connecting process easily. If the length L1 is designed longer so as to secure a lager space which is required for easy connecting process, the operation section should be longer. That is, the forceps opening side of the operation section should be longer in particular, as a result, the endoscope has a spoiled overall balance which causes a difficult operation thereof. As a result, there is a disadvantage in that the connecting process has to be carried out in an extremely small space when the conventional endoscope is assembled.

SUMMARY OF THE INVENTION

The present invention has been developed in view of the above-described circumstances, and has its aim the provision of an inner structure for an operation section of an endoscope, which makes it possible to secure a sufficient space for connecting a pipe to a tube without enlarging the length of the operation section.

To achieve the above-mentioned objects, in an inner structure for an endoscope of the present invention, the structure comprises an operation section including an opening for inserting a medical treatment means; a pipe provided inside the operation section for guiding the inserted medical treatment means into the operation section; a tube provided inside the operation section for guiding the medical treatment means into an insertion part of the endoscope; connecting means for connecting the tube to the pipe; a joint member provided inside the operation section for jointing the insertion part to the operation section; and a housing space included inside the Joint member for housing the connecting means.

In a preferable embodiment of the present invention, the connecting means comprises a first connecting member secured to an end of the pipe and a second connecting member being coupled with the first connecting member. The tube passes through the second connecting member, and the second connecting member is movable along the tube. When connecting the tube to the pipe, the second connecting member is moved along the tube to be housed in the housing space.

According to the present invention, when the pipe and the tube are connected to each other, the second connecting member is moved to be housed in the housing space which is included in the Joint member. As a result, in the present invention, the space for the connecting process can be enlarged by a length of the second connecting member. After the first connecting member is inserted into the end of the tube, the second connecting member is taken out from the housing space to be coupled with the first connecting member, so that the tube can be connected to the pipe.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DESCRIPTION OF THE PREFERRED EMBODIMENT

Detailed description will hereunder be given of the preferred embodiment of a structure of an at-hand operation section of an endoscope according to the present invention with reference to the accompanying drawings.

Figure 1:
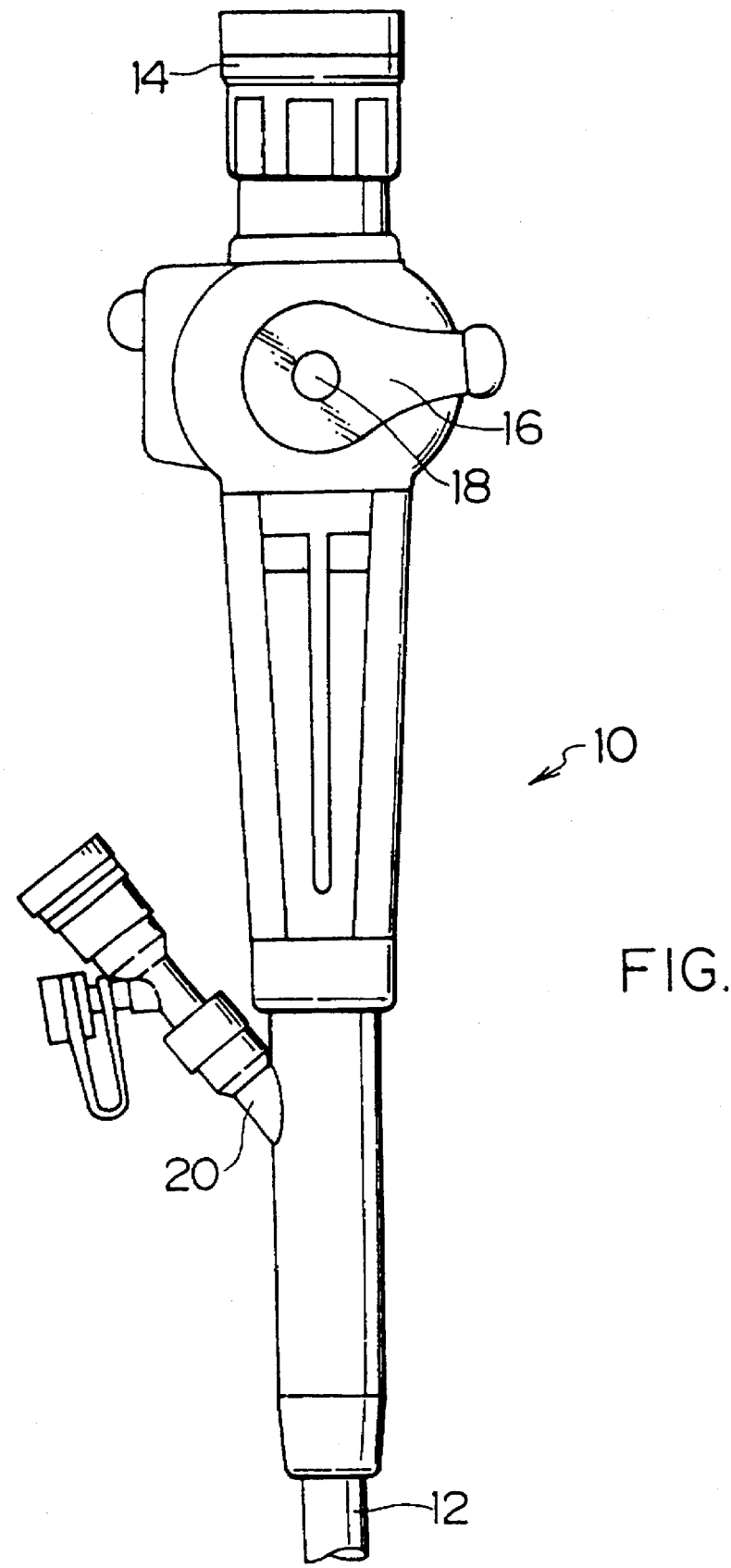
FIG. 1 is an external view illustrating an operation section of an endoscope applying thereto an inner structure for an operation according to the present invention.

FIG. 1 is an external view illustrating an operation section of an endoscope applying an inner structure for an operation section according to the present invention thereto. As shown in FIG. 1, an insertion part 12 is connected to a bottom end of the operation section 10, and an eyepiece 14 is formed at a top end of the operation section 10. A lever 16 for bending operation is provided in the proximity of the eyepiece 14.

The lever 16 is rotatable on an axis 18. A forceps opening 20 is formed in the operation section 10 on the insertion part 12 side.

Figure 2:
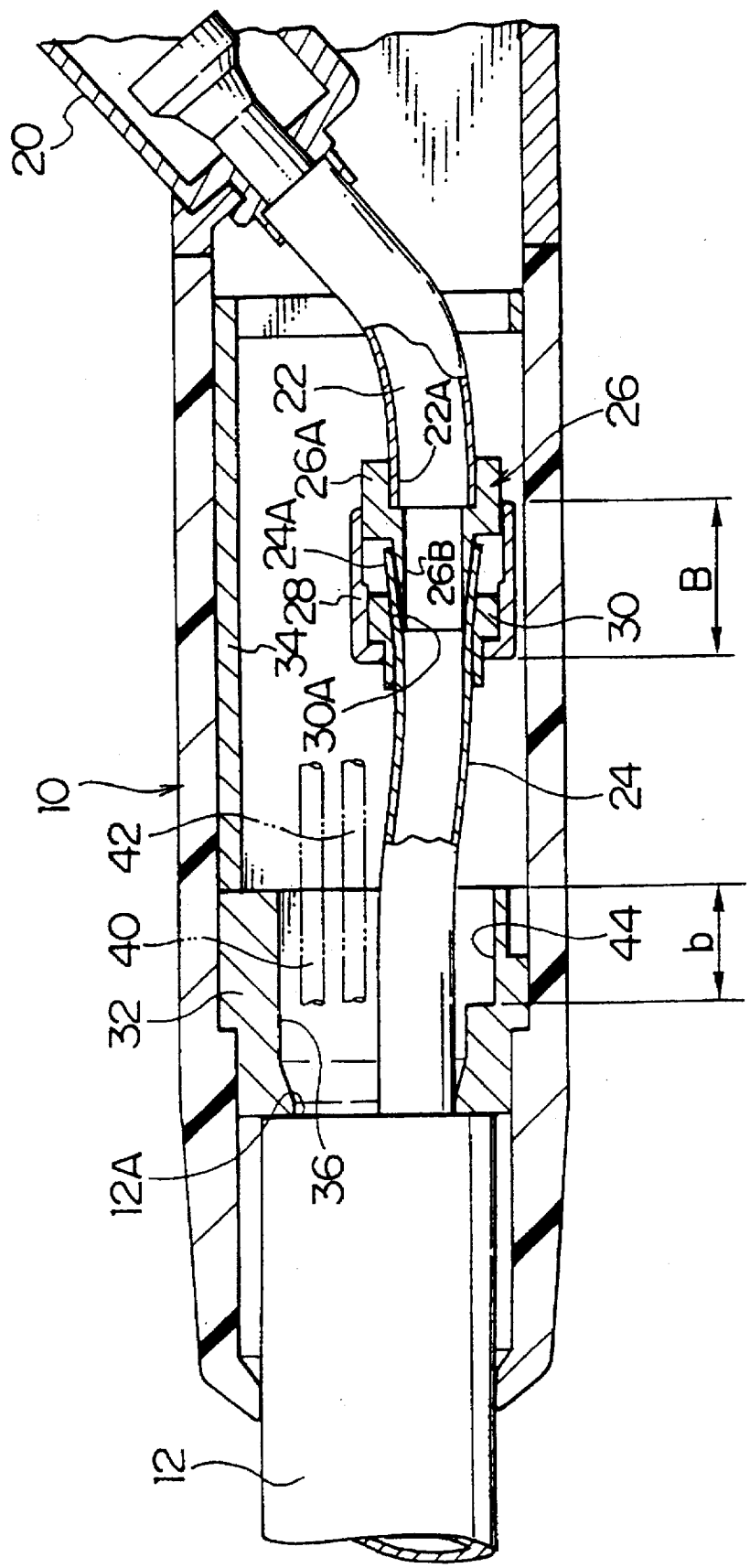
FIG. 2 is a sectional view illustrating essential parts of the operation section in FIG. 1.

A pipe 22 is connected to the forceps opening 20 as shown in FIG. 2. The pipe 22 is curved so that its end portion 22A can face the insertion part 12. A medical treatment means such as a biopsy forceps, etc. (not shown in the drawing) is inserted from the forceps opening 20 and guided into the operation section 10. The medical treatment means is guided up to the forward end of the insertion part 12 by a flexible tube 24.

The pipe 22 and the tube 24 are connected to each other by a first connecting member 26 and a second connecting member 28. The first connecting member 26 is cylindrical and has a convex(T)-shape in cross section, that is, the member 26 includes a base portion 26A of a large diameter (right side of FIG. 2) and a projected portion 26B of a small diameter (left side of FIG. 2). The base portion 26A is secured to an end 22A of the pipe 22. The projected portion 26B is tapered so as to be easily inserted into an end 24A of the tube 24.

Figure 4:
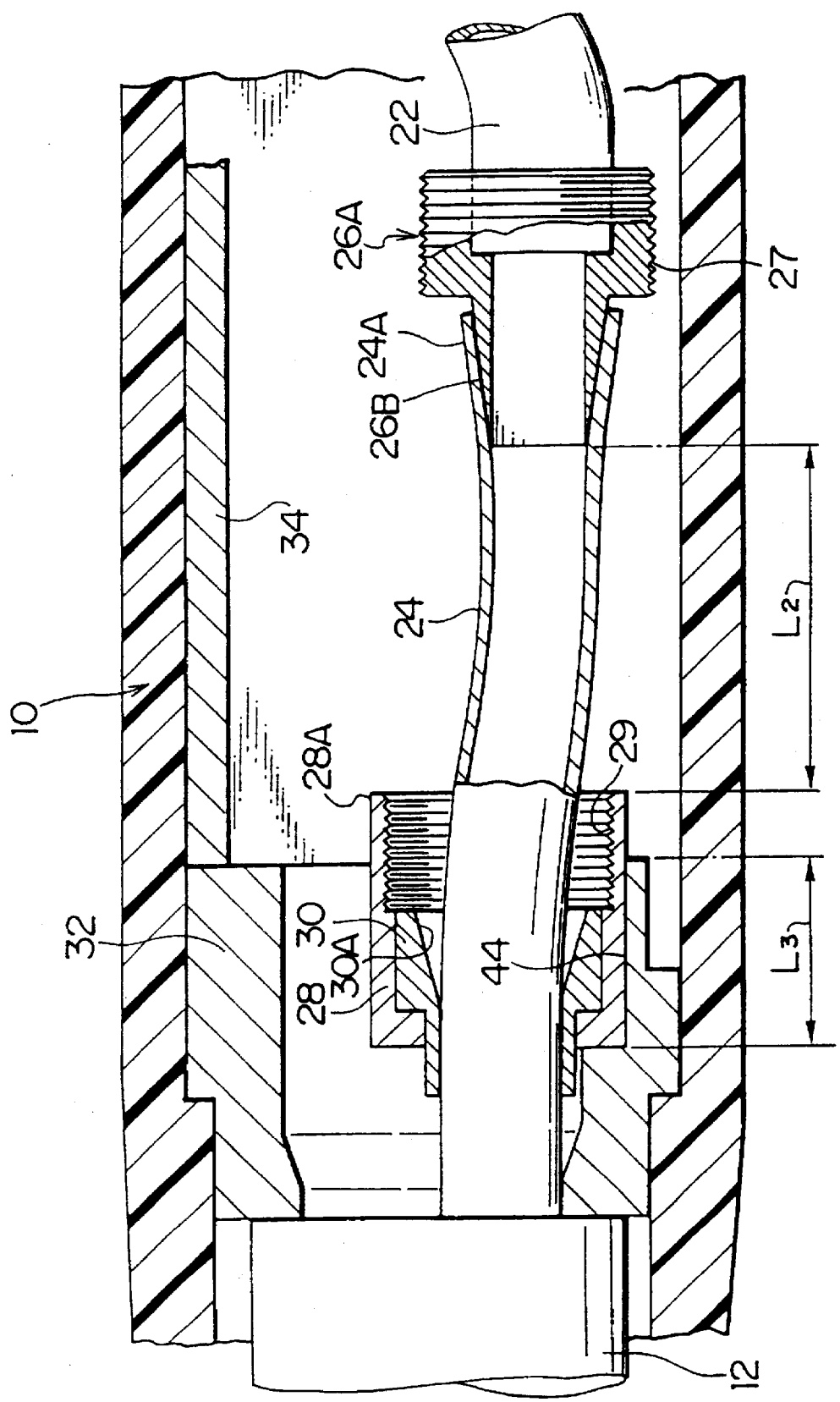
FIG. 4 is an enlarged sectional view illustrating a state that a second connecting member is housed in the joint ring.
Figure 5:
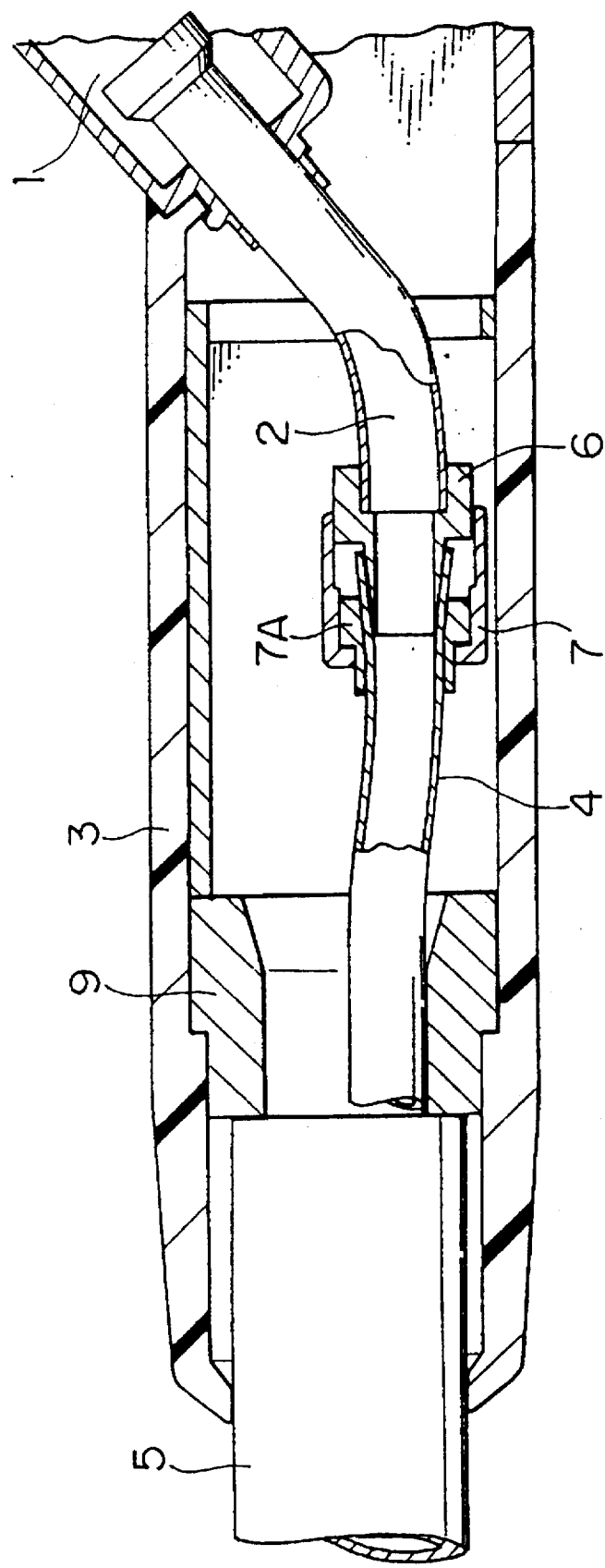
FIG. 5 is a sectional view illustrating essential parts of the operation section of a conventional endoscope.

The second connecting member 28 is formed like a cylinder. The tube 24 is made to pass through the second connecting member 28. As shown in FIG. 4, a female screw part 29 is formed on an inner wall of the second connecting member 28 so as to be engaged with a male screw part 27 formed on the base portion 26A of the first connecting member 26. An inner ring 30 is secured to the inside of the second connecting member 28. The inside of the internal diameter of the ring 30 gradually increases in such a manner to have a wider diameter at the first connecting member 26 side as shown in FIG. 4. When the tube 24 is coupled to the projected portion 26B of the first connecting member 26 and the first connecting member 26 is screwed into the second connecting member 28, the tube 24 is held between the tapered projected portion 26B and an inner ring 30 of the second connecting member 28. As a result, the pipe 22 and the tube 24 are connected to each other.

A joint ring 32 is provided inside the operation section 10 for connecting the insertion part 12 to the operation section 10. That is, the joint ring 32 is connected to a Joint 34 which is a frame of the operation section 10 and to an end 12A of the insertion part 12. The tube 24, a light guide 40, a tube 42 for sending air and water (these are described in FIG. 2 with a two-dot chain), an absorption tube, etc. enter into the insertion part 12 from the operation section 10 through an inner space 36 of the joint ring 32.

Figure 3:
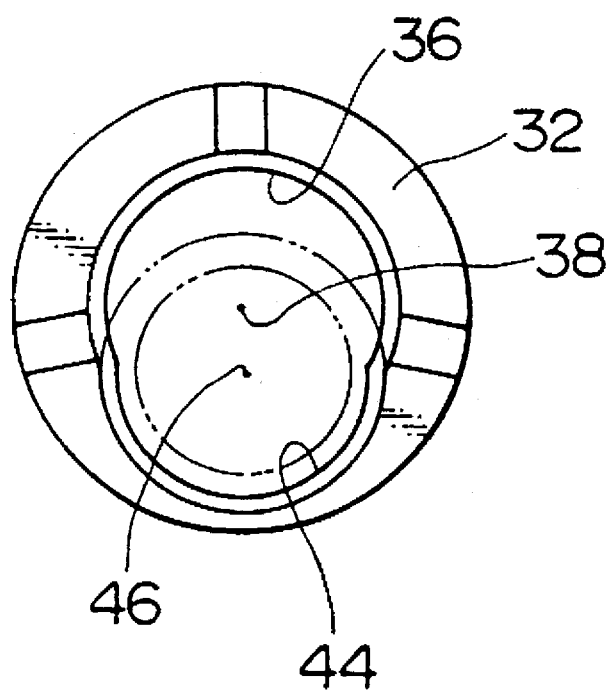
FIG. 3 is a plan view illustrating a joint ring.

As shown in FIG. 3, the joint ring 32 includes a round housing space 44 which is hollowed out from the inner space 36. A center 46 of the curvature for the housing space 44 is shifted from a center 38 for the inner space 36, that is, the center 46 is at a position away from a center 38 by a predetermined distance downward in FIG. 3. The radius of curvature for the housing space 44 is designed to be slightly larger than that for the outer periphery of the second connecting member 28. Also, the depth of the housing space 44 is designed to be slightly smaller than the length B of the second connecting member 28. Accordingly, as shown in FIG. 4, the second connecting member 28 can be housed in the housing space 44 of the joint ring 32 except for the end 28A. As a result, the space for connecting (L2) is large compared with the conventional endoscope by the length L3 which is obtained by housing the second connecting member 28 in the housing space 44.

Next, an explanation will hereunder be given of a process for connecting the pipe 22 to the tube 24 in the inner structure of endoscope which is constructed in the above-mentioned manner.

First, the end of the tube 24 is cut appropriately in such a manner to secure a length by which the projected portion 26B of the first connecting member 26 is inserted therein. Next, the tube 24 is made to pass through the second connecting member 28 and the inner ring 30. The second connecting member 28 together with the ring 30 is moved toward a Joint ring 32 along the tube 24, and housed in the housing space 44 of the joint ring 32 as shown in FIG. 4. As a result, the length L2 of the space for connecting is secured.

Next, the end 24A of the tube 24 is coupled to the projected portion 26B of the first connecting member 26. Then, the second connecting member 28 is taken out from the housing space 44, and is moved toward the first connecting member 26 along the tube 24. Then, the first connecting member 26 is screwed into the second connecting member 28, so that the end 24A of the tube 24 is held between the projected portion 26B of the first connecting member 26 and the ring 30 of the second connecting member 28. As a result, the process for connecting the pipe 22 to the tube 24 is complete.

Figure 6:
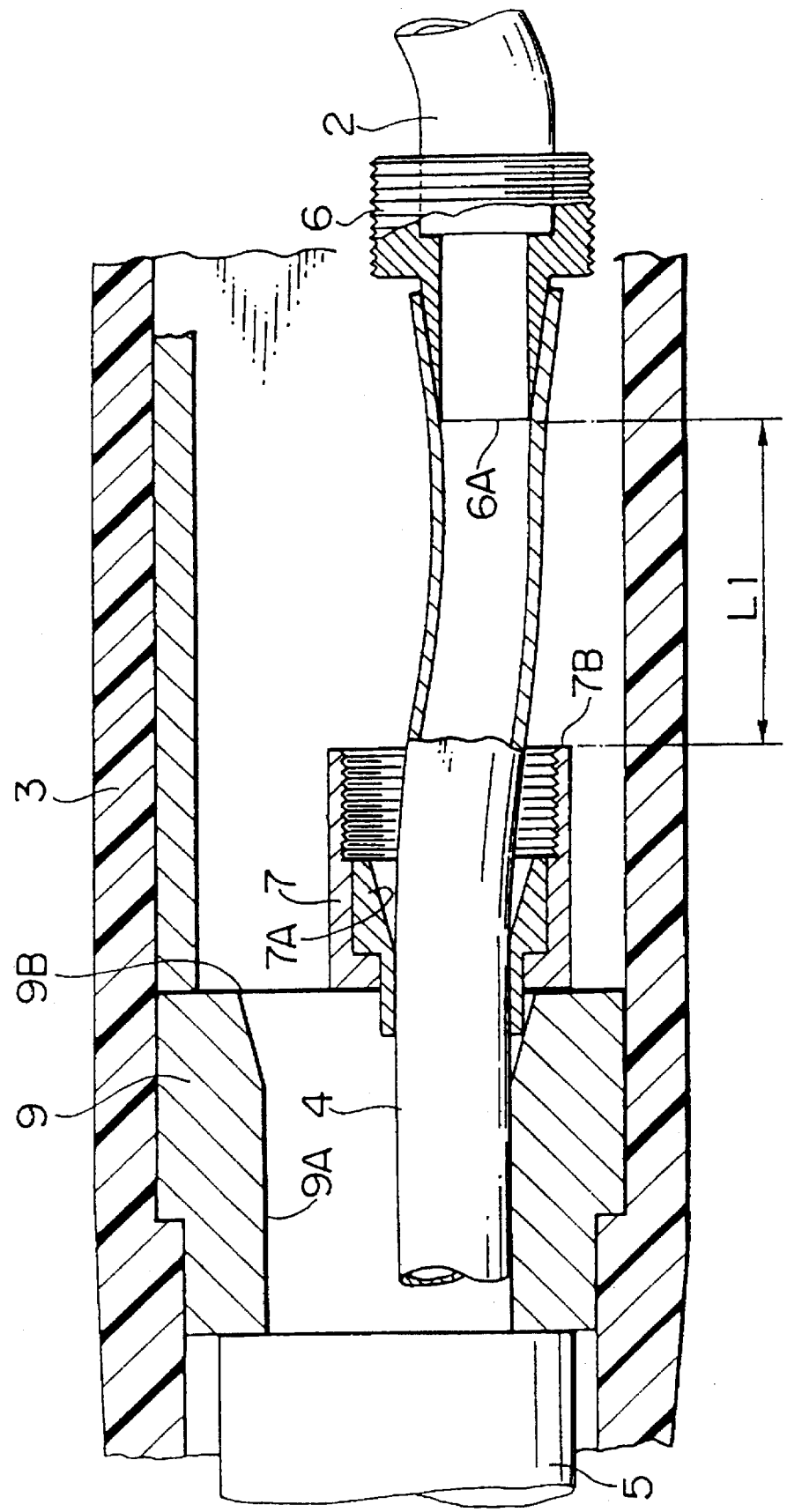
FIG. 6 is an enlarged sectional view illustrating a space for connecting a pipe to a tube of the conventional endoscope of FIG. 5.

As has been described above, the second connecting member 28 is housed in the housing space 44 which is formed in the joint ring 32 in this embodiment, so that the length L2 of the space for the connecting space can be larger than the conventional length L1 (see FIG. 6) by a length L3 of the housing space 44. As a result, even though the operation section 10 is not long, it is possible to secure the sufficient length of the space for the connecting process.

Moreover, in this embodiment, by designing the space 44 in such a manner that an axis of the first connecting member 26 is an extension of an axis of the second connecting member 28 housed in the space 44, the tube 24 hardly moves even if the second connecting member 28 is moving. Therefore, the other members (the light guide, the tube for sending air and water, the absorption tube, and the image guide, etc.) do not shift from a set position, so it is possible to prevent the members and the tube 24 from interfering with each other and being cut.

In this embodiment, the explanation was given of the structure in which the pipe 22 for guiding the forceps is connected to the tube 24. However, the present invention is not be limited to this, and can be applied to the structure in which a pipe for sending air water and absorption is connected to a tube.

As has been described above, according to the inner structure for an endoscope of the present invention, a space for housing the second connecting member is formed in the joint member, and the second connecting member is moved in the direction of the joint member to be housed in the space when the pipe is connected to the tube. Therefore, the sufficient space for the connecting process can be secured even though the operation section is not long.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An inner structure for an endoscope for use with a medical treatment means, the structure comprising:

an operation section including an opening for inserting the medical treatment means;

a pipe, provided inside the operation section, for guiding the inserted medical treatment means into the operation section;

a tube, provided inside the operation section, for guiding the medical treatment means into an insertion part of the endoscope;

connecting means for connecting the tube to the pipe;

a joint member, provided inside the operation section, for jointing the insertion part to the operation section; and a housing space, included inside the joint member, for housing the connecting means.

2. The inner structure of an endoscope as set forth in claim 1, wherein the length of the housing space is the same as the length of the connecting means.

3. The inner structure of an endoscope as set forth in claim 2, wherein the housing space has a shape fitting a part of an external shape of the connecting means.

4. The inner structure of an endoscope as set forth in claim 1, wherein the connecting means comprises:

a first connecting member secured to an end of the pipe; and a second connecting member being coupled with the first connecting member, the second connecting member being movable along the tube passing therethrough to be housed in the housing space.

5. The inner structure of an endoscope as set forth in claim 4, wherein the length of the housing space is the same as the length of the second connecting member.

6. The inner structure of an endoscope as set forth in claim 5, wherein the housing space has a shape fitting a part of an external shape of the second connecting member.

7. The inner structure of an endoscope as set forth in claim 6, wherein the second connecting member has a cylindrical shape with a radius of curvature, and wherein the housing space has a round shape of which radius of the curvature is slightly larger than the radius of curvature of the second connecting member.

8. The inner structure of an endoscope as set forth in claim 7, wherein a center of the curvature for the housing space is shifted from a center of a curvature for an inner space of the joint member by a predetermined distance.

9. The inner structure of an endoscope as set forth in claim 8, wherein an axis of the second connecting member is on an extension of an axis of the first connecting member when the second connecting member is housed in the housing space.

10. The inner structure of an endoscope as set forth in claim 9, wherein the first connecting member is cylindrical and includes a tapered forward end, the tapered forward end being inserted into an end of the tube, and wherein the second connecting member includes a conical inner wall, the tube being held between the tapered forward end and the conical inner wall when the first connecting member is coupled with the second connecting member.

11. The inner structure of an endoscope as set forth in claim 10, wherein the first connecting member includes a male screw part, and wherein the second connecting member includes a female screw part, the first connecting member being screwed into the second connecting member.

* * * * *